United States Patent [19]

Steele et al.

[11] Patent Number: 4,875,520

[45] Date of Patent: Oct. 24, 1989

[54] DESICCANT HEAT DEVICE

[75] Inventors: Donald F. Steele, Cohasset, Mass.; Lawrence C. Hoagland, Center Harbor, N.H.; Christopher Kyricos, Cohasset; Peter Tolan, Scituate, both of Mass.

[73] Assignee: Airxchange, Inc., Rockland, Mass.

[21] Appl. No.: 219,834

[22] Filed: Jul. 8, 1988

Related U.S. Application Data

[63] Continuation of Ser. No. 790,198, Oct. 22, 1985, abandoned.

[51] Int. Cl.⁴ .................... F28D 19/00; B01D 53/06
[52] U.S. Cl. ........................... 165/10; 55/387; 55/390; 55/388
[58] Field of Search ............... 55/387, 388, 389, 390; 165/10

[56] References Cited

U.S. PATENT DOCUMENTS

| | | |
|---|---|---|
| 3,085,548 | 4/1963 | Sheehan . |
| 3,664,095 | 5/1972 | Asber et al. ............... 55/387 |
| 3,671,282 | 6/1972 | Goffe . |
| 3,702,049 | 11/1972 | Morris, Jr. ............... 55/387 |
| 3,713,281 | 1/1973 | Asker et al. ............. 55/387 |
| 4,391,616 | 7/1983 | Imamura ................. 55/390 |
| 4,392,908 | 7/1983 | Dehnel . |
| 4,432,409 | 2/1984 | Steele ...................... 165/10 |
| 4,595,403 | 6/1986 | Sago et al. ............... 55/389 |

FOREIGN PATENT DOCUMENTS

| | | | |
|---|---|---|---|
| 133855 | 1/1979 | German Democratic Rep. ... | 55/390 |
| 19548 | 2/1979 | Japan ..................... | 55/390 |

Primary Examiner—Albert W. Davis, Jr.
Attorney, Agent, or Firm—Schiller, Pandiscio & Kusmer

[57] ABSTRACT

A rotary regenerative heat wheel having a heat exchange matrix comprised of a spirally wound strip of plastic having a coating of dry desiccant affixed thereto. The quantity of desiccant affixed to the strip is selected so that the sensible and latent heat transfer efficiencies of the wheel are relatively high and approximately equal. An apparatus and method are disclosed for applying a desiccant coating to a sheet of plastic.

17 Claims, 2 Drawing Sheets

DESICCANT HEAT DEVICE

This is a continuation of application Ser. No. 790,198, filed Oct. 22, 1985, and now abandoned.

This invention relates to rotary regenerative heat exchange devices and, more particularly, to heat devices having both moisture exchange and heat recovery capabilities.

The advent of increased fuel costs has resulted in greater efforts to seal air leaks in homes and other human occupancies in order to conserve energy. However, the reduction of natural ventilation has resulted in poorer quality air in these structures. A study by the National Institute of Health indicates that 50% of the illness in the United States can be attributed to the poor quality of indoor air. (See National Institute of Health Study "National Center for Health Statistics", U.S. Department of Health and Human Services, National Health Survey (Washington, D.C. 1981) As a consequence, there exists a conflict between energy conservation measures and human health factors that can best be resolved with energy efficient mechanical ventilation.

Heat recovery devices, typically in the form of rotary air-to-air heat exchangers, are well-known for their ability to transfer heat, water vapor, or both between incoming and outgoing ventilation airstreams so as to conserve energy, while at the same time improving the quality of the indoor air. Passages formed in the media comprising the heat exchange matrix permit passage of gases through the wheel. Use of these devices in ventilating, heating and/or air conditioning systems can reduce heating and cooling costs, while providing fresh outdoor air to lower internal air pollution levels. For regenerative devices of the rotary wheel type, the incoming airstream is directed through one sector of the slowly revolving wheel while an outgoing airstream is directed through another sector of the wheel. Heat and moisture are simultaneously absorbed from the warmer airstream at the one sector and removed from the wheel by the cooler, dryer airstream at the other sector. For stationary periodic flow regenerators, the airstream is alternately directed through the entire exchange device first in one direction and then in the opposite direction.

Known heat transfer devices have been described as falling into one of three categories: (1) those designed primarily for the removal of sensible heat, (2) those designed primarily for the removal of latent heat, and (3) those designed to remove both sensible and latent heat, the so-called "enthalpy exchangers". Examples of sensible heat wheels of the first category are disclosed in U.S. Pat. Nos. 2,563,415 and 4,432,409. Examples of latent heat wheels of the second category are disclosed in U.S. Pat. Nos. 2,700,577 and 3,176,446. Examples of enthalpy exchangers are disclosed in U.S. Pat. Nos. 3,307,617, 3,664,095, 3,733,791, 4,172,164, and 4,255,171.

The sensible and latent wheels of the first and second categories are limited in their application since they primarily perform only a single exchange function. With increasing fuel costs, exchange of both latent and sensible heat is desired for ventilation air.

The choice of media comprising the heat exchange matrix of the device must be suitable for application in ventilation systems for houses, offices, and other human dwellings. For example, the use of asbestos, as disclosed in U.S. Pat. No. 3,307,617, for the exchange media is undesirable.

To maximize the benefit of operating an air exchanger in conjunction with a ventilating, heating and/or cooling system, it is desirable to choose as the heat exchange matrix, a material capable of providing high sensible and latent heat exchange efficiencies. The use of metal, wool, uncoated metal strips, certain coated Kraft papers, and other fibrous cellulose materials tend to be unsatisfactory because the latent heat exchange efficiency of these materials is relatively poor, as compared to the sensible heat exchange efficiency. Several of the prior art wheels coat a "liquid" desiccant, such as lithium chloride or calcium chloride, onto the heat exchange matrix. Liquid desiccants are often undesirable however, because the wet surfaces tend to collect dust and fine particulate matter and the desiccant coating can be washed away during routine cleaning of the wheel. Also, under certain adverse operating conditions liquid desiccants can drip off the wheel.

To avoid these problems as encountered with liquid type desiccant materials, it has been suggested that a Kraft or other fibous paper may be coated with a dry desiccant material by first coating the paper with a resinous film and then applying the desiccant particles to the uncured resinous film, allowing them to imbed partially into the resin. Finally, the resin is cured to provide a permanent bonding of the desiccant particles to the treated paper surface. (See, for example, U.S. Pat. No. 3664095.) With this type of construction, a large fraction of the desiccant particle surface area is not able to absorb or adsorb moisture because it is imbedded in the relatively thick resinous coating.

Prior art enthalpy exchangers have tended to avoid the use of plastic (i.e., high molecular weight, synthetic polymers) as the medium comprising the heat exchange matrix because of difficulty in attaching the desiccant in a manner providing the desired latent heat exchange efficiency, although plastic, on the other hand, is considered a desirable medium for a heat exchange matrix because of its low cost, its high sensible heat transfer efficiency when configured in a compact regenerator design, its resistance to biological degradation, its high strength to weight ratio, and, because of its non-moisture adsorption characteristic, its safety from a human health standpoint.

One of the principal objects of this invention is to provide a relatively inexpensive heat exchange device for transfer of both sensible and latent heat at relatively high efficiency from air streams in heating, cooling or ventilating systems.

Other objects of the present invention are to provide a desiccant heat device having the desired heat and moisture transfer effectiveness; and to provide such a desiccant heat wheel in which the heat transfer medium is a plastic strip, thereby achieving the attendant aforementioned benefits of plastics (compactness, low cost, and freedom from potential adverse health effects).

Yet further objects of this invention are to provide a method of affixing a dry desiccant coating to a plastic strip without the addition of a third element, such as a thickness-adding adhesive or coating; and more particularly to provide a method of coating a polystyrene or other plastic strip with a dry desiccant so that only a relatively small portion of the surface area of each discrete desiccant particle is rendered ineffective by the bond to the plastic.

Still a further object of this invention is to provide an apparatus for efficiently bonding a dry desiccant coating to a plastic surface.

And another object of the present invention is to provide an method of wetting dry desiccant particles with a liquid useful as a solvent for applying the particles to a plastic surface.

Other objects of the present invention will in part be obvious and will in part appear hereinafter. The invention, accordingly, comprises the product possessing the features, properties and relation of components, the process including the several steps and the relation of one or more of such steps with respect to each of the others, and the apparatus possessing the construction, combination of elements and arrangement of parts, all of which are exemplified in the following detailed disclosure and the scope of the application of which will be indicated in the claims.

For a fuller understanding of the nature and objects of the present invention, reference should be had to the following detailed description taken in connection with the accompanying drawings, wherein;

FIG. 1 is a plan view, partially cut-away, of a rotary regenerative heat wheel of the type described in U.S. Pat. No. 4,432,409, modified in accordance with the present invention, herein described.

Figure 1:
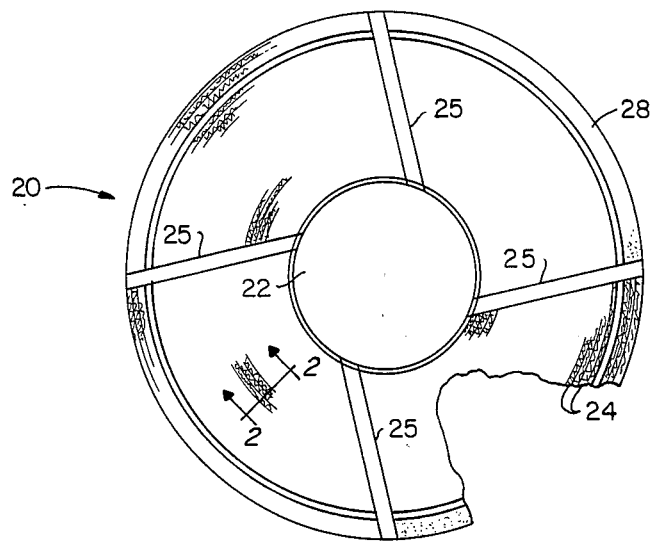

The rotary regenerative heat wheel 20 shown in FIG. 1 is identical to the wheel shown in U.S. Pat. No. 4,432,409, except that it has been modified in accordance with the present invention, so as to provide an enthalpy exchanger type heat transfer wheel. Specifically, wheel 20 includes hub 22 about which is wound one or more thin plastic strips 24 of sheet material, forming the medium of a heat exchange matrix. Preferably, a pair of strips 24a and 24b are provided, with one of the strips 24a being formed with dimples or protrusions 32 and the other strip 24b being flat. A plurality of radial spokes 25 are secured at one of their ends to hub 22, at the other of their ends to outer casing or air seal 28, and along their length to strips 24.

Figure 2:
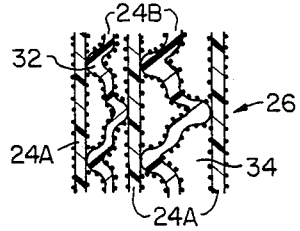
FIG. 2 is a cross-sectional view taken along line 2—2 of FIG. 1 of the wound layers of the matrix of the wheel shown in FIG. 1.

The method of making the rotary regenerative heat wheel as thus far described is known, as illustrated in the aforementioned U.S. Pat. No. 4,432,409. Briefly, however, strips 24a and 24b of selected plastic are first wound together about hub 22, so that the strips 24a and 24b form alternate layers, as described in U.S. patent application Ser. No. 320,305, filed Nov. 12, 1981 and abandoned in favor of U.S. continuation application, Ser. No. 714,685, filed Mar. 21, 1985. Radial spokes 25 are then affixed to wheel 20 to provide needed lateral stability. The spokes can be oriented along the radial lines of the wheel, or alternatively at an angle to the radial lines as shown in U.S. Pat. No. 4,432,409. As shown in FIG. 2, the dimples 32 extend in both directions from the plastic strip 24a for separating the strip 24a from the adjacent courses of the flat strip 24b when the strips are spirally wound onto the hub 22, so as to form air channels 34 for the flow of incoming and outgoing air through the wheel. Strips 24 can be made of a variety of synthetic polymers, such as polystyrene, vinyl, polyester, or the like, with biaxially-oriented polystyrene being preferred principally because of its heat sealing characteristics and its relatively low cost.

Figure 3:
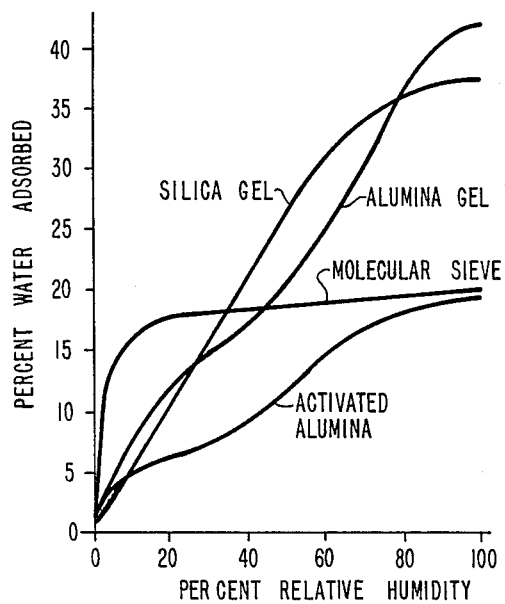
FIG. 3 is a chart containing graphs of the relative moisture adsorbing capacity of various dry desiccants.

According to the present invention, each strip 24 is coated, preferably on both surfaces with dessicant 26 (one layer of which is shown in greatly enlarged detail in FIG. 2). Several dry desiccants may be used in coat 26 in the heat wheel in the present invention, with silica gel and alumina gel being examples. As illustrated in FIG. 3, dried silica gel and dried alumina gel have, as compared to molecular sieves and activated carbon, superior moisture adsorption per unit weight over the relative humidity range of atmospheric air typically encountered during the air conditioning season. It is believed that the adsorptive capacity of the porous desiccants is primarily a function of the surface area of the desiccant. Silica gel is thus preferred, in part, over alumina gel because of the former's large surface area per unit of mass (800 square meters per gram for silica gel as compared to 300 square meters per gram for alumina gel). Silica gel also has a slightly greater adsorptive capacity as compared to alumina gel, and silica gel is readily available at a reasonable cost. Other desiccants that could be advantageously employed include various molecular sieves.

It is desirable to coat the gel onto the heat exchange matrix as a very thin layer on both sides of the plastic strip 24 to maximize the moisture-adsorbing kinetics of the desiccant. In this configuration, water molecules carried in the air flowing through the narrow channels 34 formed between layers of the strip 24 are always in close contact with the layer of desiccant 26. This close contact minimizes the diffusion path length, thereby encouraging the rapid adsorption of water vapor. Good results relating to the moisture exchange capability of the heat wheel are achieved where silica gel particles of average diameter of about 10 to 30 microns are applied to plastic strips approximately three quarters of an inch (0.75 inch) wide so as to provide a coating of silica gel having an average thickness in the range of about 10 to about 30 microns, although it will be evident that the dimensions can vary to suit the heat exchange matrix dimensions.

The desiccant is affixed by treating the surface of the plastic with a selected liquid solvent so as to dissolve the plastic surface to a minor depth so that the particles of silica gel can be applied and become bonded to the surface. The solvent, while partially dissolving the surface of the plastic to a minor depth, preferably is otherwise chemically non-reactive with the plastic. Two solvents found particularly suitable for dissolving the surface of polystyrene, while remaining otherwise chemically non-reactive, are chloroform and tetrahydrofuran (THF). Other solvents may be equally suitable. Of course, different plastic strip materials will require the use of other suitable solvents. "Liquid solvent" as used herein includes liquids with or without a solid suspending phase.

Several methods can be used for attaching particles of desiccant to solvent-treated plastic. In one method, the solvent treated surface is dusted with particles of desiccant. In another method, a slurry of desiccant and a carrier, preferably the solvent, is formed. The strip is then dipped in the slurry or the slurry is sprayed onto the strip.

In the present invention, the preferred method of applying the desiccant, however, includes the step of drawing the strip through a damp mixture of powdered desiccant and solvent. The term "damp mixture of powdered desiccant and solvent", as used above, can be described as a mixture having just enough solvent to cause the surfaces of the desiccant to be wet, but not enough solvent to fill completely the interstitial volume between particles of the desiccant. This damp powder has a consistency similar to that of damp sand. For a silica gel/THF mixture, approximately one part by volume of solvent is mixed with three parts of desiccant to form the damp powder. The proportion of solvent to desiccant is critical to the coating method of the invention. An insufficient quantity of solvent produces poor bonding and an excessive quantity of solvent produces distortion of the plastic strip.

Because of the difficulty of mixing a desiccant "powder" and a liquid, such as the solvent, to obtain even coating of the desiccant particles without the particles lumping together, as is the case when the interstices between the particles are filled with solvent, in accordance with one aspect of the present invention, solvent and desiccant are place together in a predetermined proportions and then placed in a sealed container. It was discovered that if the solvent and desiccant are mixed in the correct predetermined proportions, (e.g. for silica gel and THF, wherein one part solvent by volume is added to three parts desiccant) in a sealed container, and the container agitated for a predetermined time (typically from one to four minutes) so as to accelerate heat and pressure build up within the container. Then the sealed container is allowed to cool, and then is opened, all of the desiccant powder will be substantially evenly wetted (i.e., coated) with the solvent and the desiccant mixture ready for use. It is believed, although not proven, that when the container is sealed and the contents agitated, the heat of adsorption released by the solvent as the solvent is rapidly adsorbed by the desiccant powder causes at least a portion of the solvent to evaporate into a vapor phase throughout the container, which in turn further raises the temperature within the container This in turn causes the pressure to rapidly rise to about 10 psi, where substantially all of the liquid solvent is vaporized. In this regard, therefore, it is believed that the same results might be achieved if the liquid solvent and particles are mixed in their predetermined proportions, and heated within the sealed container with an external heater so as to raise the temperature and pressure to the desired levels (a pressure of about 10 psi) to allow substantially all of the liquid in the container to vaporize and distribute evenly thoughout the particles. In either case, whether heat is provided internally by heat of adsorption, or externally by a separate source of heating, when allowed to cool the solvent condenses to its liquid phase and is substantially evenly distributed throughout the desiccant so as to substantially evenly coat the desiccant particles without loss of solvent to the atmosphere. Alternatively, the mixture can be mechanically mixed in an open container for an extended period of time to achieve a similar desiccant/solvent distribution, in which case solvent is lost to the atmosphere.

Figure 4:
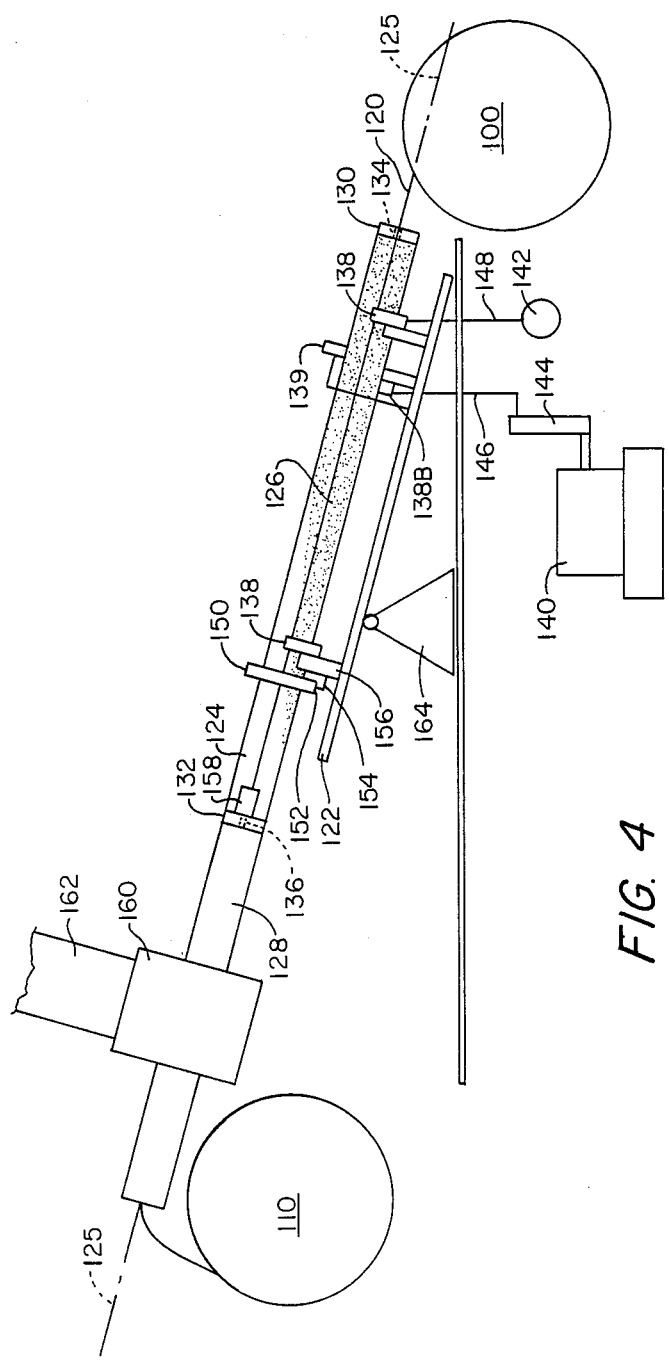
FIG. 4 is a front elevation view of the apparatus of the invention used for applying desiccant to a strip of plastic.
Figure 5:
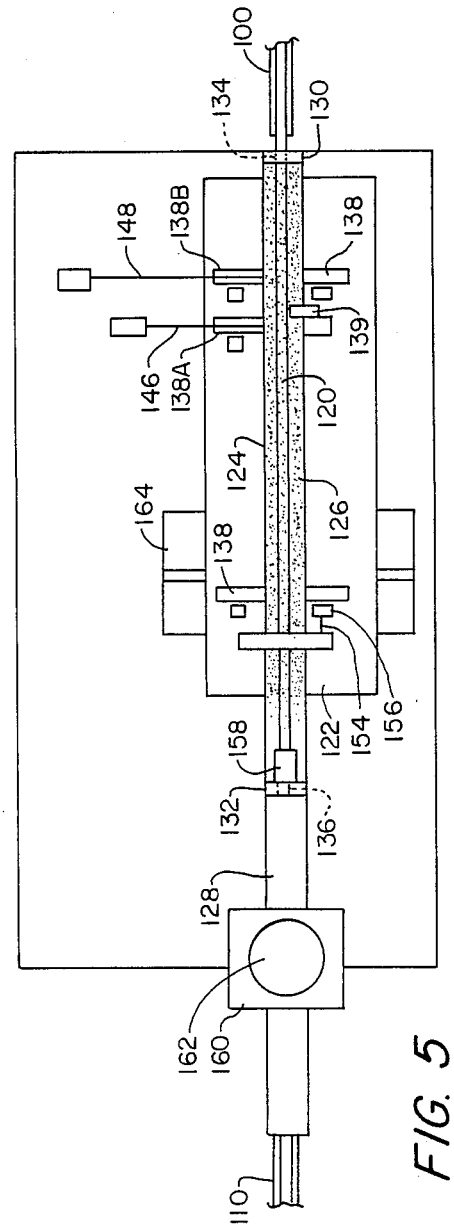
FIG. 5 is a plan view of the apparatus.

Apparatus for applying a desiccant coating to a single strip 120 of plastic, shown in FIGS. 4 and 5, includes a supply 100 of plastic strip, preferably in the form of a dispensing wheel and a take up drive 110, upon which the finished strip (strip 24 with desiccant 26) is wound. The apparatus also includes a frame 122 for supporting the hollow container or tube 124 (containing the desiccant/solvent mixture 126) for oscillatory rotation about its axis 125 of elongation, and hollow evaporating tube chamber 128 for supplying drying air to both sides of the strip 120 for evaporating solvent from mixture 126 applied to the strip. Although one strip 24 is shown as passing through the apparatus of FIGS. 4 and 5, more than one strip can be processed though the apparatus at one time, as described in greater detail hereinafter.

Preferably, tube 124 is constructed of a clear material to permit observation of the coating process. Tube 124 has removable ends 130 and 132 for supplying mixture 126. Slits or apertures 134 and 136 are formed in ends 130 and 132, respectively, on the axis 125 for passing strip 120 into and out of tube 124 along its axis 125. The slits are sized to retain mixture 126 inside of tube 124 while permitting free movement of strip 120 through the slits.

A plurality of wheels 138, for rotatably supporting tube 124, are rotatably mounted at various locations on frame 122. Tube 124 rests on top of portions of wheels 138 and is biased downwardly against wheels 138 by wheel 139. The tube 124 is rotatably driven alternately in one direction then the other about its axis 125 by drive wheel 138A and by drive wheel 138B. This alternating rotation of tube 124 continually agitates mixture 126 to distribute the solvent throughout the mixture and prevent "channeling", a condition which would otherwise arise when, after removing a quantity of damp mixture of powder and solvent, an empty passageway forms within the mixture surrounding the strip because the caking tendency of the mixture discourages adjacent mixture from filling in the passageway. Also, continuous mixing is required since the solvent is usually depleted faster than the desiccant so that in the absence of such mixing, as the strip moved through the solvent desiccant mixture, the mixture adjacent to the strip would become too dry to properly adhere to the plastic. A constant mixing action also provides for even distribution of solvent that may be added during the coating process to "make-up" for the more rapid depletion of solvent.

Means are provided for counter rotating drive wheels 138A and 138B, preferably in the form of an electric motor 140 and counterweight 142. Crank arm 144 is affixed to and driven by the output shaft of motor 140. Line 146 is affixed to wheel 138A, and when arm 144 is in the (12 o'clock) position shown in FIG. 4, line 146 is wound about wheel 138A. When motor 140 rotates arm 144 toward the position diametrically opposed from that shown in FIG. 4 (the 12 o'clock position being shown), line 146 is unwound from wheel 138A, causing wheel 138A to rotate in one direction. Rotatably driven wheel 138A rotatably drives tube 124 by frictional engagement. As driven wheel 138A rotatably drives tube 124, tube 124 rotatably drives frictionally engaged wheel 138B. When wheel 138B is driven in this manner, line 148, affixed at one end to counterweight 142 and at the other end to wheel 138B, is wound about wheel 138B. The relative driving/driven relationships are reversed as the arm 144 continues its rotational travel from the diametrically opposed position back toward the position shown in FIG. 4. Specifically, counterweight 142 causes line 148 to unwind from wheel 138B thereby rotatably driving wheel 138B in the opposite direction. Wheel 138B rotatably drives tube 124 in the same opposite direction. Tube 124 rotatably drives wheel 138A also in the same opposite direction causing line 146 to rewind about wheel 138A. When arm 144 returns to the position shown in FIG. 4, one rotation cycle is completed. This alternation of driving and driven functions between wheels 138A and 138B produces an alternating clockwise/counterclockwise rotation of tube 124 about its axis 125. Such alternating rotation is necessary to prevent twisting of strip 120 as it is pulled from the supply 100, through tube 124 by the take up drive 110, as would occur if tube 124 were rotated in just one direction. While the drive means described above is the preferred means for rotating tube 124, other means can be advantageously used. For instance, a collar having a V-groove formed in the peripheral surface thereof could be affixed to tube 124. A reversible electric motor could then drive the collar through a drive belt mounted on the motor's output shaft.

Stop means are provided to limit the arc through which tube 124 rotates to a preselected number of degrees (typically to 360 degrees). The stop means comprises collar 150 affixed to tube 124 to rotate therewith, finger 152 affixed to collar 150, and stop 154 affixed to support 156 attached to frame 122. Finger 152 is positioned on collar 150 so that when arm 144 is adjacent the twelve o'clock position, as shown in FIG. 4, finger 152 contacts one side of stop 154. When arm 144 is adjacent the six o'clock position, finger 152 contacts the opposite side of stop 154. The size and position of finger 152 and stop 154 are selected to limit the rotational arc to a chosen number of degrees.

Wiper means 158 is provided for removing excess mixture from strip 120. Means 158 is positioned adjacent end 132 so that removed mixture 126 can fall back into tube 124 for reapplication. Plastic, cloth, or other suitable materials, not affected by the solvent, can be used for the manufacture of means 158.

Evaporation tube chamber 128 includes a box 160 and tube 162 for drawing dry air through tube 128 to the box 160. Tube 128 is connected to box 160 so that air is supplied to both sides of the strip 120 as it passes through the tube 128. Tube 128 is attached to rotate with tube 124 in a suitable manner to prevent stretching of the edges of the softened plastic strip as it emerges from the alternately rotating slit 136. Suitable means, not shown, are provided in box 160 to permit tube 128 to rotate relative to the box. Tube 128 has open ends with a frame supported slit, not shown.

The tube 124 is preferably supported at an angle by support 16,, adapted to support the frame 122 at a selected location. The angle of inclination of tube 124 can be varied by moving support 162 so as to contact frame 122 at various locations. Since tube 124 is generally not completely filled with mixture 126, moving support 160 toward dispensing wheel 100 causes mixture 126 to accumulate at end 130 thereby decreasing the length of strip 120 exposed to mixture 126 at any one instance. Moving support 162 away from dispensing wheel 100 causes some of the mixture 126 to move toward end 132 thereby increasing the length of strip 122 exposed to mixture 126 at any one instance. It should be appreciated that exposure time of the strip to the solvent desiccant mixture can also be controlled by varying the speed of the take up wheel 110.

In operation, the tube 124 is charged with a damp powder desiccant/solvent mixture 126. The strip 120 is initially taken from dispensing wheel 100 through slits 134 into the container or tube 124, where it contacts the "damp powder", past means 158 out of the tube through slit 136, through the evaporation tube 128, through the frame supported slit of tube 128 to a take up wheel 110. During this process, the desiccant acts as a carrier of the solvent for dissolving the surface of the plastic to a minor depth and for carrying the particles into contact with the surface. Motor 140 is energized for alternately rotating tube 124 about its axis 125 so as to continuously agitate the mixture in the tube. The take up wheel 110 is driven by a motor (not shown) to pull strip 120 through the tube, while the tube is alternately rotated about its axis 125. The strip is preferably pulled at a rate of approximately one foot per second with the contact time between mixture and strip of approximately one to three seconds producing the desired desiccant bonding. This contact time is critical for proper application of the desiccant coating, since insufficient contact time will result in poor bonding, while excessive contact time causes loss of mechanical strength of the plastic with resulting distortion of the strip. The dried coating on the strip is such that only a small portion of the surface area of each discrete desiccant particle is rendered ineffective by its bond to the plastic strip. This bonding maximizes the surface area of the desiccant available for water vapor adsorption.

When coating two are more strips, such as the strips 24a and 24b of FIG. 2, both strips can be simultaneously pulled through the apparatus and wound onto take-up reel 110. In such an operation, the strips 24a and 24b are dispensed from separate dispensing wheels 100 into container 124. Preferably, each strip 24 enters through a separate slit, similar to slit 134, so that the strips lie in the same or parallel planes and are spaced from one another as they enter the container 124. The strips pass through the container in a spaced apart relation so that both sides of each strip will be adequately coated with the mixture in the container. The coated strips preferably pass through separate spaced apart wiper means, similar to means 158, and out the tube through separate slits similar to slit 136. Both strips are dried in evaporation tube 128 and preferably passed through the frame supported slit of box 160 with one strip on top of and in contact with the other so that they are wound together by the take up wheel 110.

In practice, the solvent tends to evaporate from the mixture before the desiccant is depleted from the tube 124. When the percentage of solvent by volume drops below approximately 15%, additional solvent must be added. The time at which additional solvent should be added can be determined by observing the mixture through the clear tube 124. As the solvent by volume drops below about 15%, the desiccant starts to become dry and powdery. The used mixture can be "rewetted" with solvent using the aforementioned sealed container process. The quantity of solvent added in this "rewetting" procedure is chosen to bring the mixture back to its original one part solvent/three part desiccant proportion. Alternatively, solvent may be slowly added, for example, through the end caps of tube 124, during the coating process to replace lost solvent.

The sensible and latent heat efficiencies of the desiccant heat devices made according to this method are approximately equal. For one particular rotary heat wheel design which has been tested extensively, the sensible heat and moisture exchange efficiencies are both about 75%. Thus, the total heat content or enthalpy effectiveness of that particular wheel is about 75%. When installed in the ventilation system of an air conditioned structure, the reduction in the ventilating air cooling load on a typical warm humid day (95 degrees F. outdoor air temperature, and 73 degrees F. dew point) is about 25% due to transfer of sensible heat and about 50% due to transfer of latent heat (moisture) for a total of about 75% reduction in ventilating air cooling load. Thus, the presence of the desiccant for moisture transfer is very important to the overall energy savings under these weather conditions.

It should be appreciated that the method of the present invention and the apparatus for carrying out the method can be utilized to make other product besides the desiccant rotary heat wheel described. For example, the method can be used to make plastic stationary periodic flow regenerators. The plastic material can be in any form, such as sheet form, in a honeycomb structure, in block form, etc. Further, plastic sheets and similar materials for use in chromatography can be coated on one or both sides with a desiccant material. Where it is desirable to coat only one side of a plastic sheet or strip material, one side of the sheet or strip has affixed thereto a layer of material that does not chemically react with the selected solvent/powder mixture. As the plastic material is drawn through the mixture, the desiccant mixture will not adhere to the non-reactive layer.

It also should be appreciated that in addition to controlling the angle of tube 128 so as to control the amount of mixture to which the strip is in contact so as to control the time of exposure, the time the plastic is exposed to the solvent before the solvent evaporates in the evaporation tube 128 can also be controlled chemically. For example, a non-reactant dilutant, such as alcohol, can be added to the solvent prior to mixing the solvent with the desiccant in a sealed container. The amount of dilutant added is a function of the solvent reaction time desired. The greater the amount of dilutant by volume added to the solvent the slower the reaction time of the solvent on the plastic material.

Since certain changes may be made in the above processes without departing from the scope of the invention hereininvolved, it is intended that all matter contained in the above description or shown in the accompanying drawings shall be interpreted in an illustrative and not in a limiting sense.

What is claimed is:

1. A desiccant regenerative heat exchange device comprising at least one plastic surface coated with finely comminuted particles of dry desiccant bound to said at least one plastic surface as a consequence of dissolving to a minor depth using a selected solvent at least the portion of said at least one plastic surface contacting said particles.

2. A device according to claim 1 wherein said particles of dry desiccant are bound directly to said at least one plastic surface.

3. A device according to claim 1, wherein said device comprises at least one wound strip of plastic material having both surfaces of said strip coated with said dessicant.

4. A device according to claim 3 wherein said device includes a wheel, said wheel comprises a hub about which said strip is wound, and a plurality of spokes affixed to said hub and extending from said hub across said wound strip, said spokes being affixed along their length to a surface of said wheel for transmitting driving force from said hub to said wheel.

5. A device according to claim 3, wherein the average thickness of said desiccant coating on each surface of said strip is between about ten and thirty microns thick.

6. A device according to claim 3, wherein said strip has a plurality of regularly distributed surface protrusions for separating adjoining layers of said wound strip so as to permit the flow of atmospheric gases between said layers.

7. A device according to claim 6, wherein said device includes a second plastic strip wound with said first strip so that said first and second strips from alternate layers on said wheel, said second strip having both surfaces coated with said desiccant.

8. A device according to claim 7, wherein said second plastic strip is flat.

9. A device according to claim 3, wherein said particles are bound to said surfaces so that only a small portion of the surface area of each discrete desiccant particle is in contact with said strip.

10. A device according to claim 1, wherein said desiccant includes dried silica gel.

11. A device according to claim 3 wherein said one plastic strip is made from biaxially-oriented polystyrene.

12. A device according to claim 1, wherein said desiccant includes dried alumina gel.

13. A device according to claim 1, wherein said desiccant particles each have an average diameter of between approximately ten and thirty microns.

14. A device according to claim 1, wherein said particles of dry desiccant are bound to said one plastic surface without the use of an adhesive substance.

15. A device according to claim 1, wherein said particles of dry desiccant are embedded slightly in said one plastic surface.

16. A desiccant regenerative heat exchange device comprising at least one plastic surface coated with finely comminuted particles of dry desiccant bound directly to said at least one plastic surface, wherein said particles of dry desiccant are bound to said one plastic surface by means of a solvent bonding process.

17. A device according to claim 16, wherein said particles of dry desiccant are embedded slightly in said one plastic surface.

* * * * *

UNITED STATES PATENT AND TRADEMARK OFFICE
CERTIFICATE OF CORRECTION

PATENT NO.   : 4,875,520

DATED        : October 24, 1989

INVENTOR(S)  : Donald F. Steele, et al.

It is certified that error appears in the above-identified patent and that said Letters Patent is hereby corrected as shown below:

Claim 7, column 10, line 21, delete "from" and substitute therefor -- form --.

Signed and Sealed this

Twentieth Day of November, 1990

Attest:

HARRY F. MANBECK, JR.

*Attesting Officer*  *Commissioner of Patents and Trademarks*